United States Patent [19]
Bonati et al.

[11] Patent Number: 5,472,426
[45] Date of Patent: Dec. 5, 1995

[54] CERVICAL DISCECTOMY INSTRUMENTS

[75] Inventors: Alfred O. Bonati, New Port Richey; Philip J. Ware, Spring Hill, both of Fla.

[73] Assignee: B.E.I. Medical, Hackensack, N.J.

[21] Appl. No.: 108,036

[22] Filed: Aug. 17, 1993

Related U.S. Application Data

[63] Continuation-in-part of Ser. No. 758,013, Sep. 12, 1991, Pat. No. 5,269,797.

[51] Int. Cl.$^6$ .................................................. A61M 5/00
[52] U.S. Cl. .......................... 604/164; 606/191; 128/751
[58] Field of Search .................................. 606/191, 193, 606/194, 197, 198, 199; 128/751, 754, 753, 752; 604/22, 161–165, 169, 170

[56] References Cited

U.S. PATENT DOCUMENTS

| | | | |
|---|---|---|---|
| 4,396,021 | 8/1983 | Baumgartner | 128/751 X |
| 4,449,532 | 5/1984 | Storz | 606/191 |
| 4,674,502 | 6/1987 | Imonti | 128/751 X |
| 4,699,611 | 10/1987 | Bowden | 606/191 X |
| 4,862,891 | 9/1989 | Smith | 606/191 |
| 4,981,482 | 1/1991 | Ichikawa | 606/191 X |
| 4,986,825 | 1/1991 | Bays et al. | 128/751 X |
| 5,071,410 | 12/1991 | Pazell | 606/191 X |
| 5,158,543 | 10/1993 | Lazarus | 606/191 X |
| 5,217,479 | 6/1993 | Shuler | 128/751 X |

FOREIGN PATENT DOCUMENTS 0390528  10/1990  European Pat. Off. ............... 128/751

*Primary Examiner*—Chris A. Bennett
*Attorney, Agent, or Firm*—Joseph C. Mason, Jr.; Ronald E. Smith

[57] ABSTRACT

Arthroscopic cervical discectomy instruments include a push knob for a guide wire, a pair of telescopically mounted dilator tubes, one of which includes a water port so that the tube provides the additional function of an irrigation tube, a ligament cutter, a continuous suction punch, a cervical osteotone, a cervical cureet, a nucleus extractor and a cureet nucleus extractor. The dilator tubes, the ligament cutter, and the continuous suction punch are all centrally bored to receive the guide wire. All of the instruments are of arthroscopic proportions and each instrument, exclusive of its handle, is slideably insertable through the bore of the largest in diameter dilator tube. The largest in diameter dilator tube serves as a dilator, an irrigation tube, and as the main sheath through which the other tools are inserted. In a second embodiment, the pair of dilator tubes are replaced with a plurality of telescoping dilator tubes of progressively larger diameters and shorter lengths. The tools enable a novel dilation method and a novel surgical method.

3 Claims, 10 Drawing Sheets

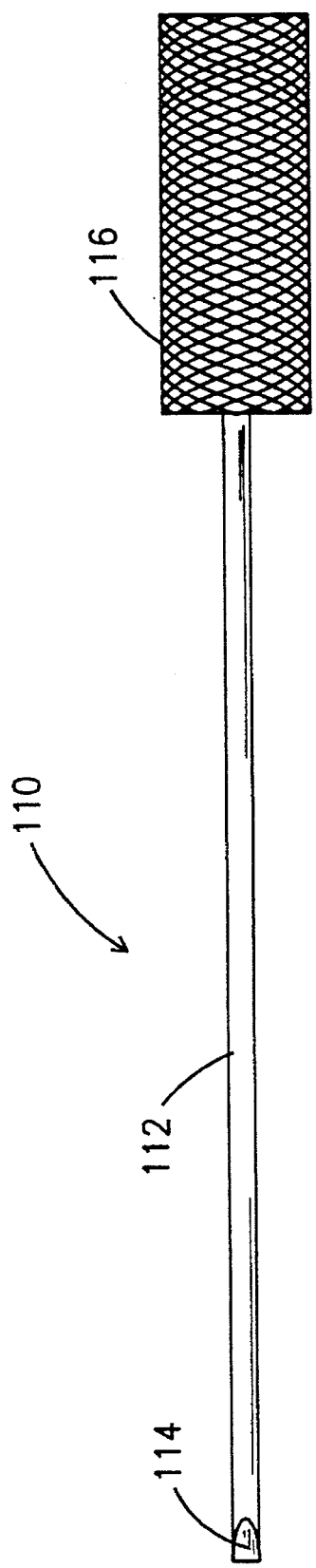
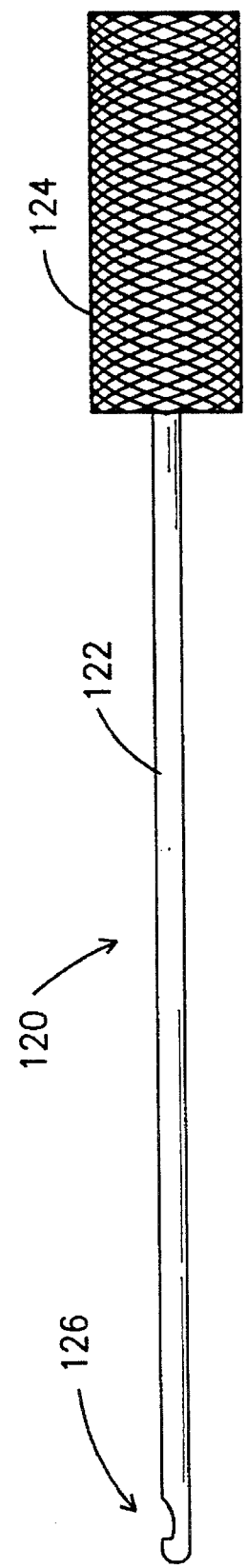
Fig. 7
Fig. 8

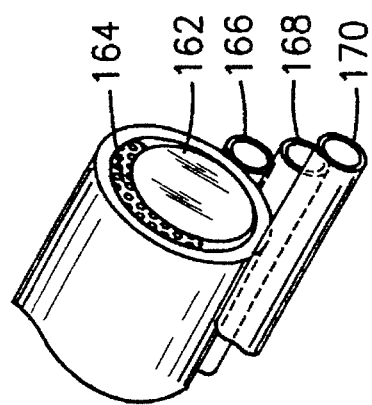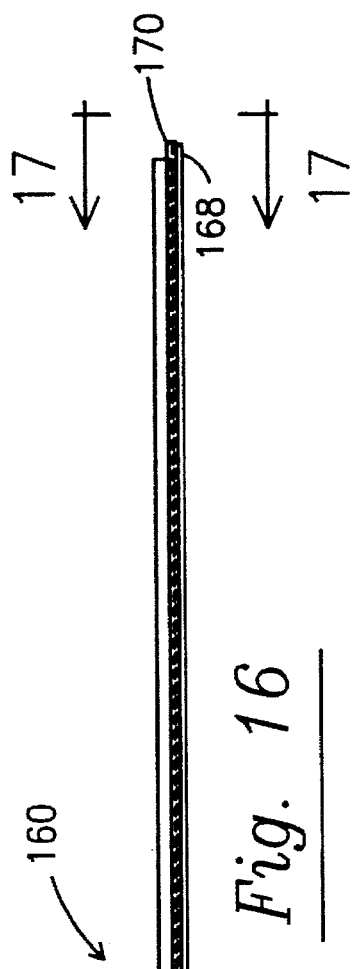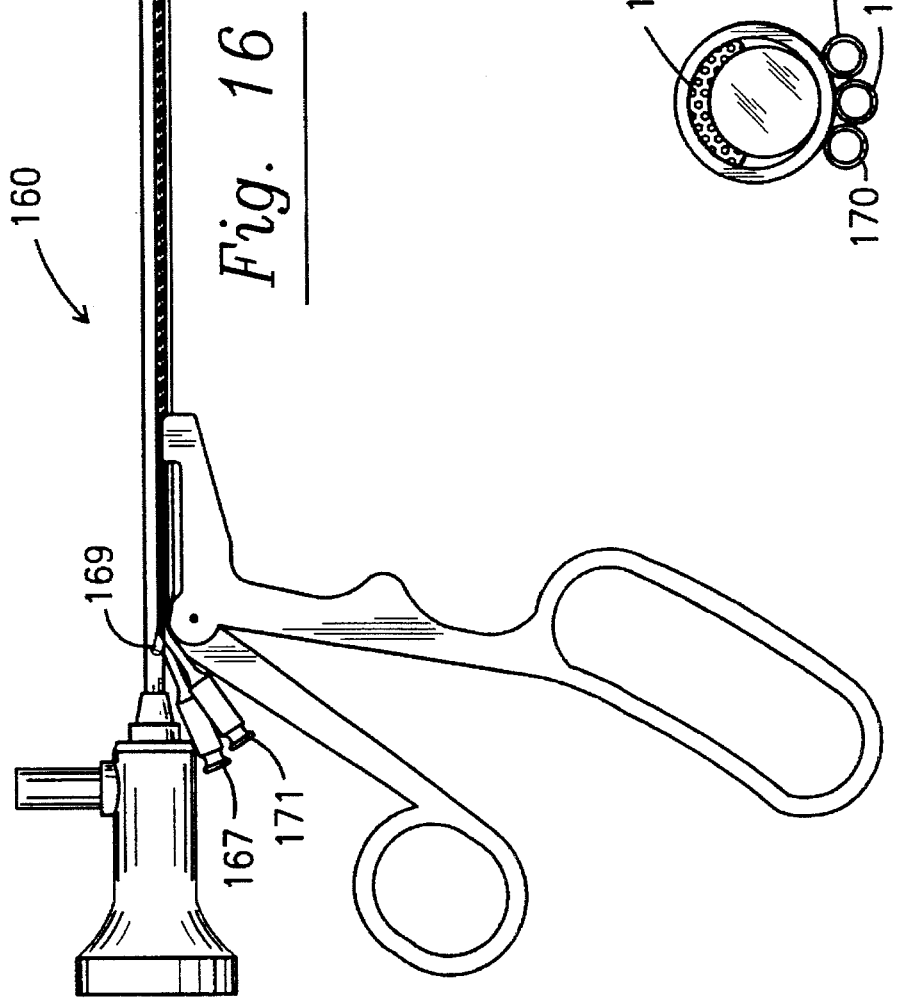

CERVICAL DISCECTOMY INSTRUMENTS

CROSS-REFERENCE TO RELATED DISCLOSURE

This disclosure is a continuation-in-part of a disclosure filed Sep. 12, 1991, bearing Ser. No. 07/758,013, by the same inventors, now U.S. Pat. No. 5,269,797, entitled "Cervical Discectomy Instruments."

BACKGROUND OF THE INVENTION

1. Field of the Invention

This invention relates to novel arthroscopic surgical instruments and novel methods for their use. More particularly, it relates to miniature tools having utility in connection with methods for performing a cervical discectomy.

2. Description of the Prior Art

Neck pain is sometimes caused by the pressure of a ligament bearing against the spinal cord. The pressure can be surgically relieved by debulking, i.e., removing some of the nucleus beneath the ligament so that the ligament can return to its normal position.

In highly invasive, i.e., non-arthroscopic surgery, nucleus debulking is performed by making a relatively large incision and cutting through the membrane that overlies the ligament and through the ligament in order to reach the nucleus. The nucleus is cut and sufficient amounts thereof are removed to thereby remove pain-causing pressure.

In arthroscopic surgery, a small incision is made and the incision is dilated so that surgical tools may be introduced therethrough. More particularly, after the initial incision is made, a dilator tube is introduced thereinto to increase the diameter of the incision. The dilator tube in common use has a rather large inside diameter so that it can accept the various arthroscopic tools that are introduced thereinto as the operation proceeds.

In arthroscopic surgery, one of the tools usually employed to debulk the nucleus is known as a punch tool because it operates something like a paper punch, i.e., a shearing action accomplishes the desired cutting. More particularly, a typical punch tool has an elongate neck and the shearing mechanism is positioned at the distal end of that neck. A pair of handle members at the proximal end of the neck are squeezed by the surgeon and the squeezing action causes a first part of the shearing mechanism to slide with respect to a stationary second part of that mechanism, and nucleus matter between said parts is sheared from the main body of nucleus matter.

The cervical discectomy punches of the type just described operate in a batch mode, i.e., they shear a single piece of tissue for each entry through the incision to the surgical site. After each shearing action, the punch is withdrawn, an irrigation tool is inserted to irrigate the site and place the sheared piece of nucleus into suspension, the irrigation tool is withdrawn, a suction tool is inserted to vacuum the irrigation fluid and the sheared piece, the suction tool is withdrawn, and the punch tool is inserted for another shearing action. Thus, a surgeon might be required to make dozens of entries and exits through an incision in the course of a surgical procedure when using a conventional, one bite punch instrument. Such multiple entries, exits, and re-entries obviously extend the time required to perform the surgical procedure, and tire the surgeon and surgical assistants.

Since arthroscopic surgical techniques require much smaller incisions than highly-invasive surgery, they permit much faster patient recovery and reduce the length of hospital stays and save the expenses associated therewith. However, there is a need for an improved method of dilating the initial incision so that tissue trauma arising from dilation is minimized. Moreover, improved instruments and surgical procedures are needed.

There is also a need for an improved multiple function tool for performing multiple functions such as laser irradiation, irrigation, suction, and the like so that multiple re-entries to the surgical site can be minimized.

The prior art, however, when considered as a whole at the time the present invention was made, neither taught nor suggested to those of ordinary skill in this field how the dilation process could be improved, how the known arthroscopic tools could be improved, or how the debulking procedure itself could be improved.

SUMMARY OF THE INVENTION

A novel set or kit of miniature tools is provided for use by arthroscopic surgeons so that cervical discectomy can be performed arthroscopically for the first time.

Importantly, the novel kit includes plural dilator tubes having progressively shorter lengths and progressively greater diameters; they are used in a second embodiment of the novel method to gradually dilate an arthroscopic incision to minimize the trauma to tissue. When the final dilator tube is in position, a novel multiple function tool having a relatively large outside diameter may be used advantageously.

In the performance of both embodiments of the novel method, the procedure begins with the making of a small, arthroscopic incision. A stylet having a removable inner tube disposed concentrically within an outer barrel is then inserted through the incision, and the inner tube of the stylet is withdrawn, leaving the barrel in position.

A first tool enables the physician to properly position a guide wire, known as a K wire, relative to the nucleus to be debulked. The K wire, with the aid of said first tool, is inserted through the bore of the stylet barrel; it guides all of the instruments used subsequently in the surgical procedure to the site of the procedure.

In a first embodiment of the invention, the tool employed to position the guide wire is detached therefrom after said guide wire is properly positioned and a second and third tool are provided to facilitate the initial dilation of the arthroscopic incision. The second tool is the main sheath through which all other tools are inserted throughout the course of the first embodiment of the surgical procedure and may also serve as the irrigation tool so that the operation site can be irrigated with saline solution as needed.

In the second embodiment, the second and third tools are not employed. Instead, after the first tool has been detached from the guide wire, a plurality of progressively shorter in length but progressively greater in diameter dilator tubes are employed to gradually dilate the incision. More particularly, a first long, narrow diameter tube is telescopically inserted over the barrel of the stylet to provide a very small increase in the diameter of the dilation; this allows the tissue to gradually stretch. The stylet is then withdrawn, with the first dilator tube remaining in position. A second dilator tube, having a greater inner diameter than the first, is slid over said first dilator tube to again provide a slight increase in the diameter of the incision to allow the tissue to stretch further. The second dilator tube is shorter than the first, so that the trailing end of the first dilator tube extends beyond the trailing end of the second dilator tube. Thus, the first tube is easily withdrawn by grasping its trailing end and pulling it out. A third dilator tube, shorter than the second and having an increased diameter, is then introduced over said second dilator tube, and the above-described process is continued until the incision has been dilated to the desired diameter. When the penultimate tube is withdrawn, the final tube remains in place and said final tube becomes the sheath through which all instruments are inserted as the operation progresses. All of the longer dilator tubes may be withdrawn collectively after the shortest dilator tube has ensleeved the penultimate dilator tube, i.e., the surgeon need not withdraw each preceding tube after its ensleevement by the next greater in diameter dilator tube, but may instead leave the longer but narrower in diameter dilator tubes in place until the final dilation has been achieved.

This invention further includes a ligament cutter; in the first embodiment, it is inserted through the bore of the main sheath. In the second embodiment, it is inserted through the bore of the largest in diameter dilator tube. The ligament cutter performs the function its name expresses. More particularly, it cuts through the membrane that overlies the ligament and it further cuts a passageway through the ligament to expose the nucleus material thereunder.

The novel method further employs a novel punch tool having a continuous suction port. The novel punch tool enables the physician to complete an entire debulking procedure, i.e., to perform repeated shearing actions, with a single insertion through an incision. The punch is inserted a single time, and the physician squeezes the handle members thereof as many times as needed so that the shearing members slice off as many pieces of nucleus material as required. The pieces of excised matter are continuously removed from the site by a continuous suction that withdraws irrigation fluid and surgical debris from the site. The suction means is provided in the form of an elongate suction bore that is formed in the neck of the punch; a suction port to which a cannula is releasably secured is positioned at the proximal end of the suction bore, and an opposite end of the cannula is detachably secured to a collection tank that is in fluid communication with a source of negative pressure. Suitable means are provided so that the physician can control the flow rate of the irrigation fluid through the suction bore.

An arthroscopic cervical osteotone, an arthroscopic cervical cureet, with and without handles, a batch-type nucleus extractor, and a tool having multiple functions are also disclosed; all of these tools are insertable through the main sheath (first embodiment) or the largest in diameter dilator tube (second embodiment) as and if needed.

Thus it is apparent that an important object of this invention is to provide arthroscopic surgeons with the tools they need to perform cervical discectomies.

Another major object is to disclose the surgical techniques that are enabled by the novel tools.

Still another object is to disclose a novel method of progressively enlarging an arthroscopic incision by employing a plurality of dilator tubes of decreasing length and increasing diameter.

These and other important objects, features and advantages of the invention will become apparent as this description proceeds.

The invention accordingly comprises the features of construction, combination of elements and arrangement of parts that will be exemplified in the construction hereinafter set forth, and the scope of the invention will be indicated in the claims.

BRIEF DESCRIPTION OF THE DRAWINGS

For a fuller understanding of the nature and objects of the invention, reference should be made to the following detailed description taken in connection with the accompanying drawings, in which:

FIG. 7 is a side elevational view of a novel cervical osteotone member;

FIG. 8 is a side elevational view of a novel cervical cureet;

FIG. 16 is a side elevational view of a novel combination tool;

FIG. 17 is an end view of said combination tool, taken along line 17—17 in FIG. 16;

FIG. 18 is a perspective view of the distal end of said combination tool;

Similar reference numerals refer to similar parts throughout the several views of the drawings.

DETAILED DESCRIPTION OF THE PREFERRED EMBODIMENT

Figure 1:
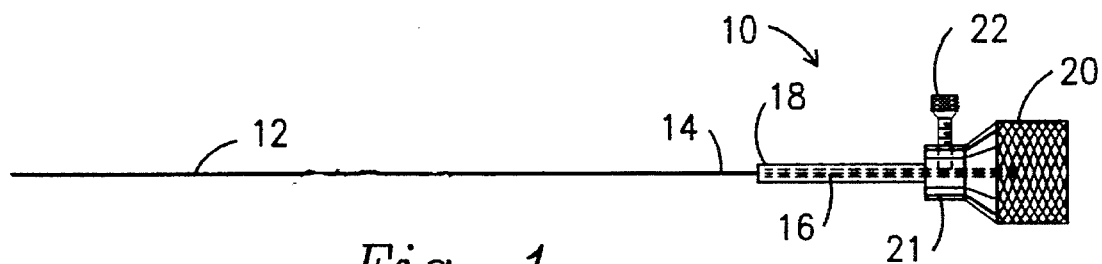
FIG. 1 is a side elevational view of a novel K-wire push knob showing a length of K-wire retained therewithin.

Referring first to FIG. 1, there it will be seen that the novel K wire push knob is denoted 10 as a whole. The proximal end 14 of K wire 12 is received within bore 16 that is formed in push knob 10. More particularly, the push knob includes a boss 18 and a knurled base 20; bore 16 extends the entire length of the boss and part of the length of the base as shown. A radially disposed set screw 22 having a knurled head screw threadedly engages an internally threaded radial bore formed in a reduced diameter part 21 of base 20, said radial bore intersecting bore 16 so that the leading end of the set screw bears against the K wire when the set screw is advanced to releasably retain the guide wire within bore 16.

Figure 20:
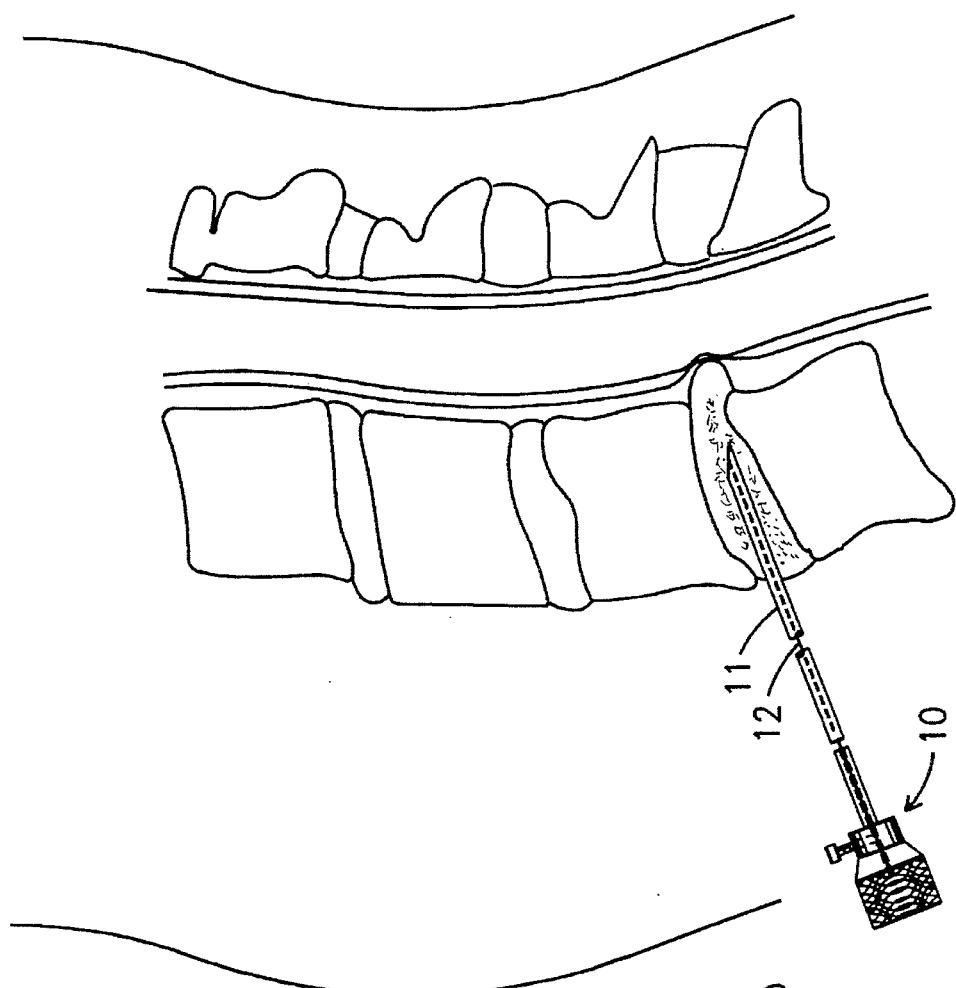
FIG. 20 is the second figure in said series.
Figure 19:
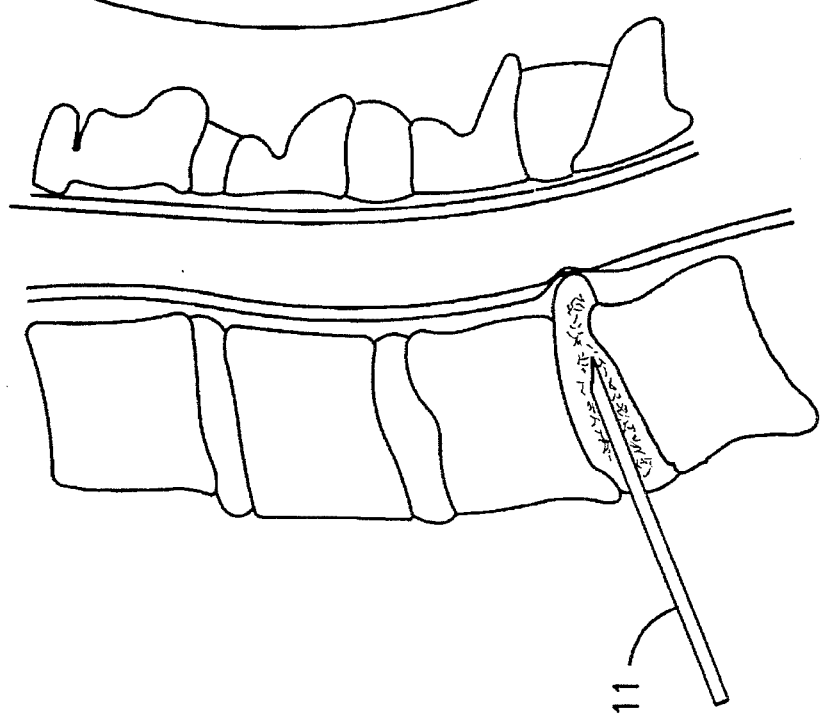
FIG. 19 is the first of a series of animations showing the steps of the novel surgical procedure, and the tools employed in such steps.
Figure 21:
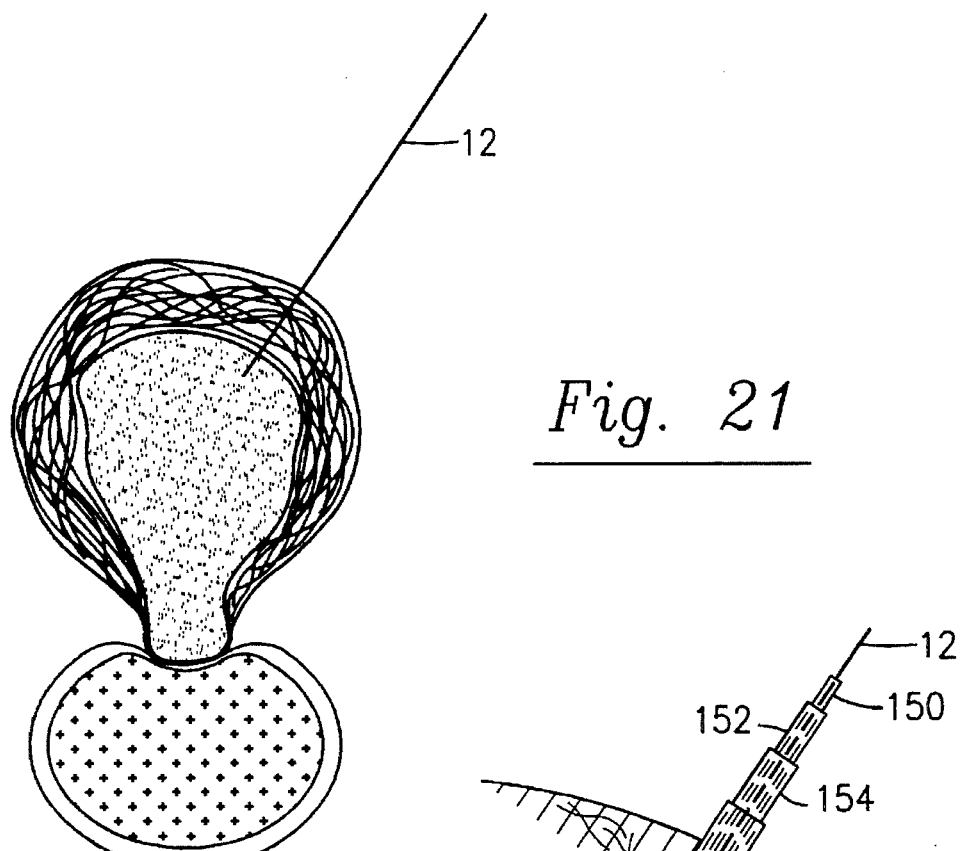
FIG. 21 is the third figure in said series.
Figure 22:
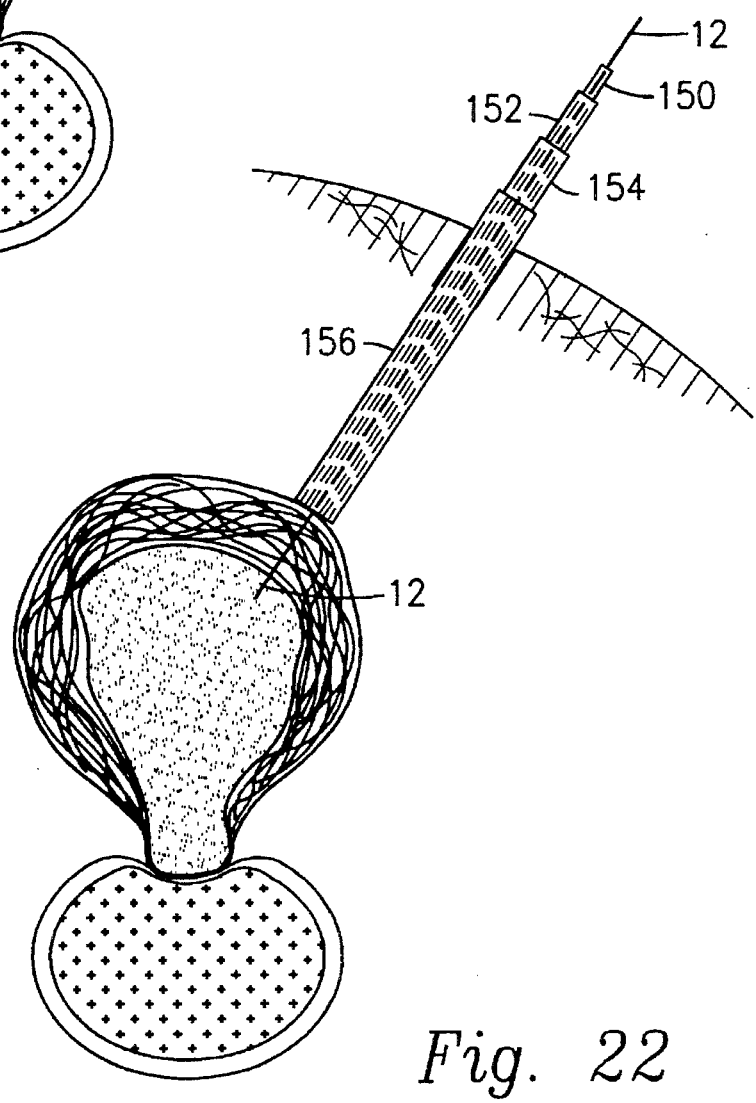
FIG. 22 is the fourth figure in said series.

After the arthroscopic incision has been made and the inner tube of the stylet has been withdrawn, the push knob is grasped by the physician and the distal end of the K wire is inserted through the barrel of the stylet into the ligament at the point where the underlying nucleus is to be debulked (see FIGS. 19 and 20). The push knob 10 is then removed from the K wire by loosening set screw 22; penetration of the distal end of the K wire into the ligament retains it in position throughout the remainder of the surgical procedure.

K wire 12 is preferably about 140 mm in length, and the overall length of push knob 10 is 24 mm. The reduced diameter part 21 of base 20 is 8 mm in length and the balance of base 20 is 12 mm in length.

Figure 2:
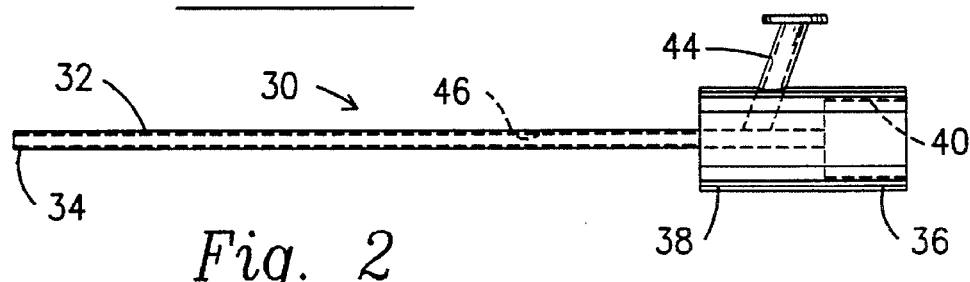
FIG. 2 is a side elevational view of a novel dilator tube having a water port.
Figure 3:
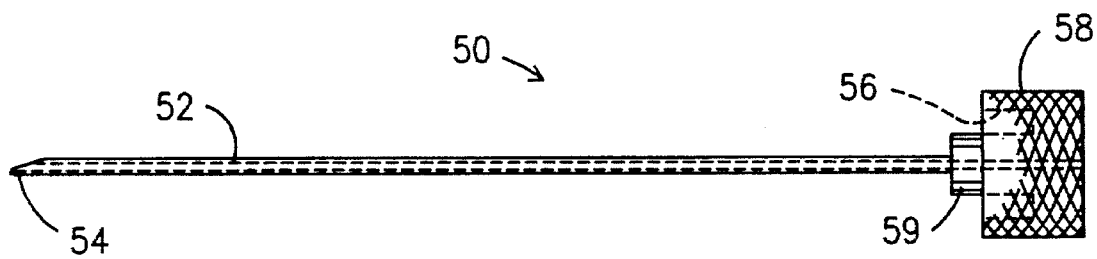
FIG. 3 is a side elevational view of a novel dilator tube.

The incision is then gradually dilated in a novel way. The dilator tube 30 of FIG. 2 and the dilator tube 50 of FIG. 3 are releasably coupled together to form a dilator means, shown in FIG. 4, as a preparatory step to the dilation. Once coupled together, they are threaded over the K wire so that they are properly positioned. More particularly, tubular part 52 of dilator tube 50 is slideably, i.e., telescopically, inserted into the hollow bore of the tubular part 32 of dilator tube 30. The dilator means thereby created is guided to the site by the K wire, i.e., the bore of tubular part 52 axially receives said K wire. Note that the distal end 54 of tubular part 52 is tapered and extends beyond the distal end 34 of tubular part 32. Note further that the proximal end 36 of base 38 of tube 30 is slideably received within circular recess 56 formed in knurled base 58 of tube 50 and that boss 59 of base 58 is slideably received within a complementally formed recess 40 formed in base 38 of tube 30. It should be noted that boss 59 extends from a bottom wall of recess 56. This provides a double lock between tubes 30 and 50.

The tapered distal end 54 of tube 50 performs the initial dilation; the taper is provided to avoid tearing the ligament as it passes through. After tube 50 has been advanced, then tube 30 is similarly advanced, i.e., it is advanced to the left as denoted by the directional arrow 42 in FIG. 4. Since tube 30 has an outer diameter only slightly greater than that of tube 50, this technique provides a gradual increase in the diameter of the incision.

Tube 30 further includes a water port 44 having an inlet means adapted to be engaged by a cannula, not shown; the opposite end of the cannula is detachably secured to a source of saline solution under positive pressure. Suitable valving means are provided so that the physician can control the flow rate of saline solution to port 44. Port 44 is in open fluid communication with bore 46 of tubular part 32 so that saline solution flowing from the source thereof is delivered to the site of the surgical procedure under the direction and control of the surgeon. Port 44 is not needed when the novel combination tool of FIGS. 16–18 is employed, because said tool incorporates a plurality of functions, including irrigation.

Figure 4:
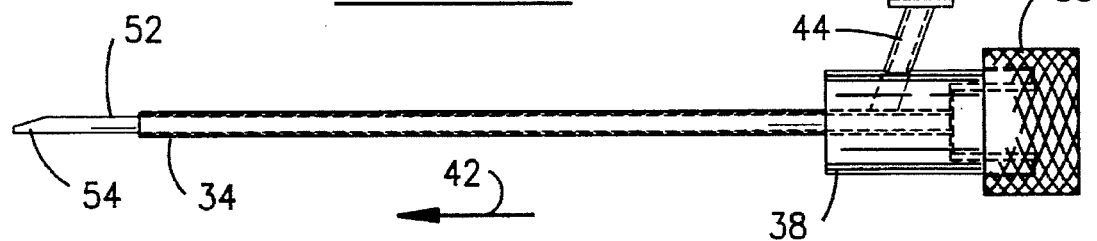
FIG. 4 is a side elevational view showing the tubes of FIGS. 2 and 3 in their assembled configuration.
Figure 11:
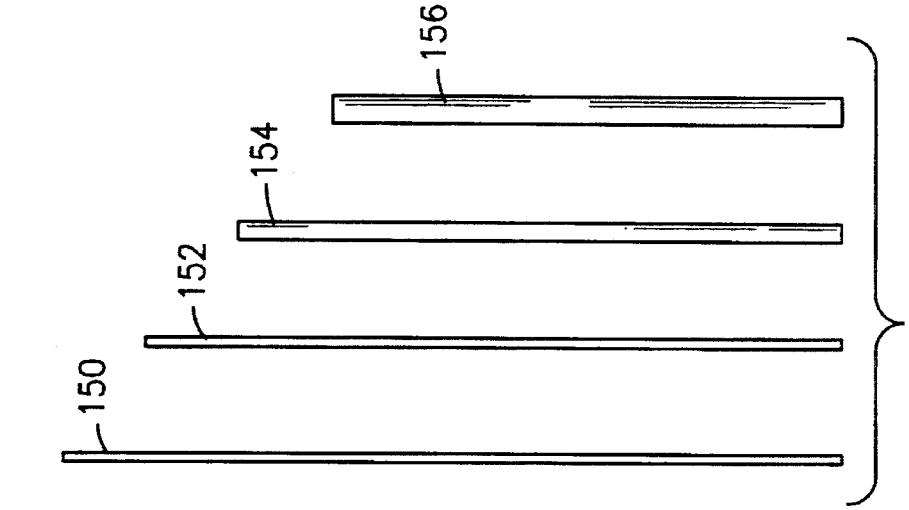
FIG. 11 depicts the dilator tubes of the second embodiment of this invention.

After dilator tube 30 has been advanced to complete the dilation of the incision, as indicated by directional arrow 42 as aforesaid, dilator tube 50 is then slidingly decoupled from the dilator means of FIG. 4 and withdrawn. In the first embodiment, dilator tube 30 which remains in position is then used as the main sheath through the bore 46 of which other instruments are inserted as the surgical procedure progresses, i.e., main sheath (dilator tube) 30 remains in position, as does K wire 12, until the surgical procedure has been completed. In the second embodiment, the dilator tubes shown in FIG. 11 are employed in the manner summarized above. In both embodiments, gradual dilation is accomplished; this technique represents a major advance over the prior art technique of performing the dilation in a non-gradual manner with a single dilator tube. It should be noted that in both embodiments, the arthroscopic instruments are inserted through the bore of the last-inserted, i.e., the largest-in-diameter and shortest-in-length dilator tube.

The inside diameter of first embodiment main sheath 30, i.e., the diameter of bore 46, is 2.5 mm, and the outside diameter of sheath 30 is 3 mm. (The inside diameter of the fourth dilator tube of the second embodiment is about 4 mm; thus, it is capable of receiving the novel combination tool). The overall length of main sheath 30 is 81 mm. The length of tubular part 52 of dilator tube 50 is 92 mm, including the 10 mm length of boss 59. Recess 40 formed in base 38 of main sheath 30 is also 10 mm in depth to receive said boss 59.

Figure 5:
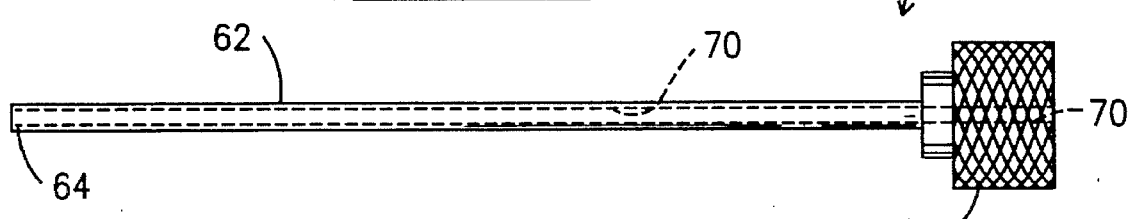
FIG. 5 is a side elevational view of a novel ligament cutter.

The ligament cutter 60 of FIG. 5 is next employed; it has an overall length of 104 mm and it includes a tubular part 62, having an outside diameter of 2.4 mm, said tubular part 62 having a leading end 64; leading end 64 has a cookie cutter-type cutting edge. Tool 60 further includes a proximal end having a 10 mm in length knurled base 66, a boss 68 having about the same length, and a bore 70 for receiving the K wire. The ligament cutter 60 is used by threading it onto the K wire, i.e., by aligning said wire with bore 70 at the leading end of the cutter and by advancing the cutter through bore 46 of main sheath 30 toward the surgical site. The physician then oscillates the cutter 60 about its longitudinal axis of rotation as indicated by double-headed directional arrow 72; this action causes cutting edge 64 to slice through the membrane overlying the ligament and continued oscillation and advancement of the cutter enable it to cut a passageway through the ligament and into the underlying nucleus. The cutter is withdrawn after the passageway has been formed, but main sheath 30 remains in position.

Figure 6:
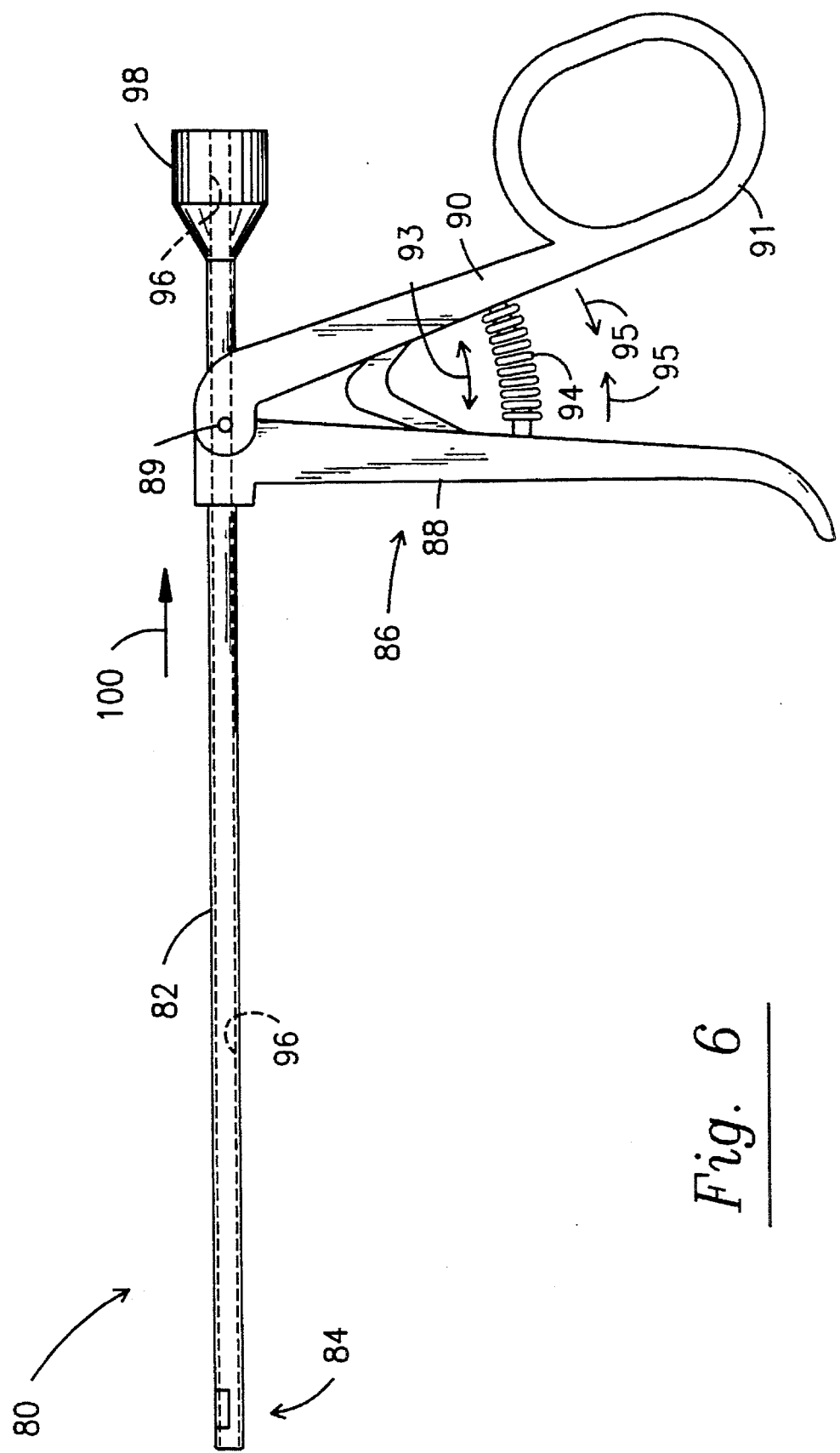
FIG. 6 is a side elevational view of the novel cervical continuous suction punch.

Debulking of the nucleus may now be undertaken; the preferred tool for performing the debulking procedure is depicted in FIG. 6 and is denoted as a whole by the reference numeral 80.

This illustrative embodiment of the novel cervical continuous suction punch 80 includes an elongate neck 82 having a pair of shearing members collectively denoted 84 at the distal end thereof. Shearing members 84 are known in larger punch tools of the type used in highly invasive, non-arthroscopic surgery, and thus their construction need not be described. A handle means 86 in the form of a pair of handle members 88 and 90 is integrally formed with neck 82 at the proximal end thereof and said handle members depend therefrom; the members are pivotally mounted about pivot point 89, and member 90 has a thumb-receiving loop 91. A strip 92 of spring steel or other suitable material biases handle members 88 and 90 apart from one another as indicated by arrow 93, i.e., the physician must overcome the bias to squeeze said handle members toward one another. Shear members 84 are spaced apart from one another when punch 10 is in repose and ultimately converge toward one another when said handle members are squeezed; a diverging motion precedes the converging motion, but, again, the particular operation of the shearing members is well known and need not be described here.

A coil spring 94 or other suitable bias means is employed to urge the handle members 88 and 90 toward one another as indicated by converging arrows 95; thus, spring steel member 92 and coil spring member 94 are first and second bias means, respectively, that oppose one another. The strength of the opposing bias means is substantially equal. This unique arrangement of parts removes play from the handle means 86 and insures that the handle members 88 and 90 will always return to their respective positions of repose when the handle means is released.

A bore 96 is formed in neck 82 and provides fluid communication between shears 84 and suction port 98 at the proximal end of punch tool 80. Bore 96 extends into port 98 as shown; port 98 provides a mounting means to which a first end of a cannula, not shown, or other suitable flexible tube means is detachably secured when the novel punch 80 is in use. The second end of the cannula is detachably secured to an unillustrated collection receptacle that is in fluid communication with an undepicted source of negative pressure.

The site of the surgical procedure is irrigated during the nucleus-shearing process by causing irrigation fluid to flow into water port 44 in main sheath 30; the inside diameter of the main sheath is sufficient to receive neck 82 of punch tool 80 and to allow sufficient space thereabout to allow the irrigation fluid to flow freely to the surgical site. Thus, as each piece of nucleus is sheared by shears 84, releasing the squeezing motion imparted to handle members 86 and 88 opens the shears and releases the excised pieces into the irrigation fluid.

Suitable means are provided to permit the physician to control the amount of negative pressure supplied to port 98 and thus the flow rate of irrigation fluid and surgical debris flowing therethrough in the direction of arrow 100.

Thus, a single insertion of neck 82 through the bore of main sheath 30 is the only insertion needed to complete the entire debulking procedure. Irrigation fluid is introduced through water port 44 throughout the entire debulking procedure, and the suction applied to port 98 is similarly continuous throughout said procedure.

Neck 82 is preferably about 105 mm in length, exclusive of handle 86; said handle 86 has a length, measured from the neck 82 to the lowermost end of handle member 88, of about 85 mm. The outside diameter of neck 82 is 2.5 mm, and the length of the movable part of the shear members 84 is 4 mm.

FIG. 7 depicts a cervical osteotone 110 that may also be inserted through main sheath 30 if chiseling of a vertebrae is required at any stage of the procedure. Osteotone 110 includes a solid rod 112 having a chisel edge 114 formed in its leading end and a knurled base member 116 fixedly secured to its proximal end. The overall length of osteotone 110 is 125 mm; the length of rod 112 is 105 mm. The lateral extent of chisel edge 114 is 2.3 mm so that the tool is easily insertable through the bore of the main sheath.

A novel cervical cureet or scoop member 120 is depicted in FIG. 8; its rod part 122 and knurled base 124 have the same dimensions as the corresponding parts of the osteotone of FIG. 7. A scoop means 126 is formed in the leading end of rod 122; it has the same construction as a conventional scoop means of the type used in non-arthroscopic surgery, but is only 2.2 mm in length. Cureet 120 is employed to scoop up the bone fragments created by bone chisel 110.

Figure 9:
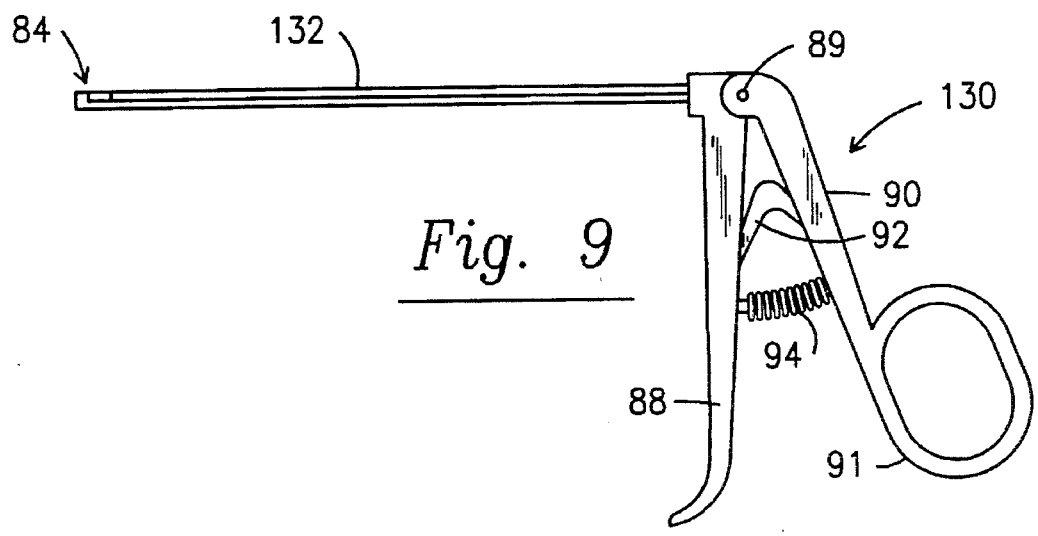
FIG. 9 is a side elevational view of a batch-type punch tool of arthroscopic dimensions that may be employed in lieu of the continuous suction punch of FIG. 6.

The punch tool 130 of FIG. 9 is like the tool of FIG. 6 in all respects except that it lacks suction port 98 and thus does not perform continuous vacuuming of the surgical site. It is suitable for use where the amount of debulking is limited. Neck 132 thereof is 105mm in length, has an outside diameter of 2.4 mm, but has no bore formed therein; shear members 84 and the rest of the parts are similar to the parts of the punch shown in FIG. 6, as indicated by the common reference numerals.

Figure 10:
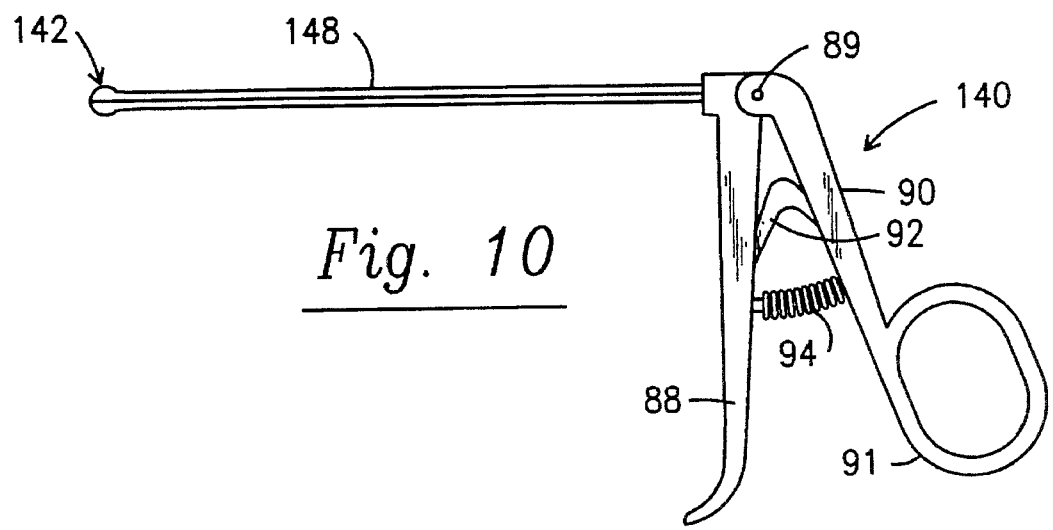
FIG. 10 is a side elevational view of a cureet tool having handle members like the handle members of the punch of FIG. 6.

Similarly, the cureet 140 of FIG. 10 has a construction like that of the punch tool of FIG. 9, but it has a distal end with scoop means 142 that is activated by squeezing handles 88 and 90. Its neck 148 is also 105 mm in length and 2.4 mm in outside diameter and it can also be inserted through the bore of main sheath 30.

All of the dimensions disclosed herein are believed to be quite critical although small deviations therefrom still fall within the scope of this important invention. The dimensions allow cervical discectomy to be performed by arthroscopic instruments. The inside and outside diameters of the dilator tubes and the outside diameters of the members insertable through the main sheath 30 are critical because they enable the arthroscopic procedures disclosed herein.

Figure 15:
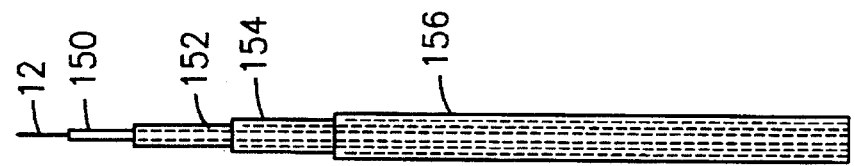
FIG. 15 depicts a fourth dilator tube having a length less than that of the third dilator tube, but having an internal diameter greater than said third dilator tube.
Figure 14:
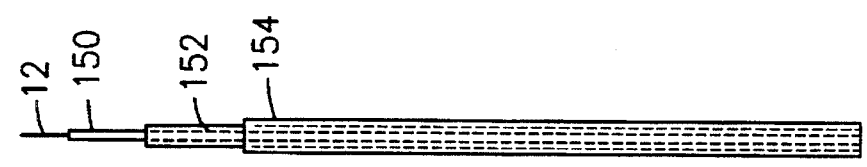
FIG. 14 depicts a third dilator tube, shorter than the second but greater in diameter, telescopically received over the second dilator tube.
Figure 13:
FIG. 13 depicts a second dilator tube, shorter but greater in diameter than the first, telescopically received over said first dilator tube.
Figure 12:
FIG. 12 depicts a first dilator tube in ensleeving relation to the outer barrel of a stylet.

In the second embodiment, the dilator tubes of FIG. 11 are used in lieu of the second and third tools. After the inner tube of the stylet has been withdrawn, dilator tube 150 is guided to the surgical site over the outer barrel of the stylet or guide wire 12, as depicted in FIG. 12. As shown in FIG. 13, larger in diameter but shorter in length dilator tube 152 is then telescoped over tube 150. Tube 150 may be withdrawn at this time, or left in place as depicted. This process is repeated with dilator tubes 154 and 156, as shown in FIGS. 14 and 15. Alternatively, the earlier-inserted tubes may be withdrawn as dilator tubes of decreasing length and increasing diameter are slipped over each preceding dilator tube, but there is no need to withdraw a dilator tube as soon as it has been ensleeved by the next greater-in-diameter dilator tube. The last-inserted dilator tube, in cervical applications, has an inner bore diameter of about four mm. In this second embodiment, all of the tools are introduced through the last-inserted dilator tube instead of through main sheath 30. In all other respects, the second embodiment is the same as the first.

Dilator tubes of larger diameters are employed in lumbar applications. Typically, the last-inserted dilator tube in a lumbar operation that follows the teachings of this invention will have an internal diameter of about ten mm.

Figure 25:
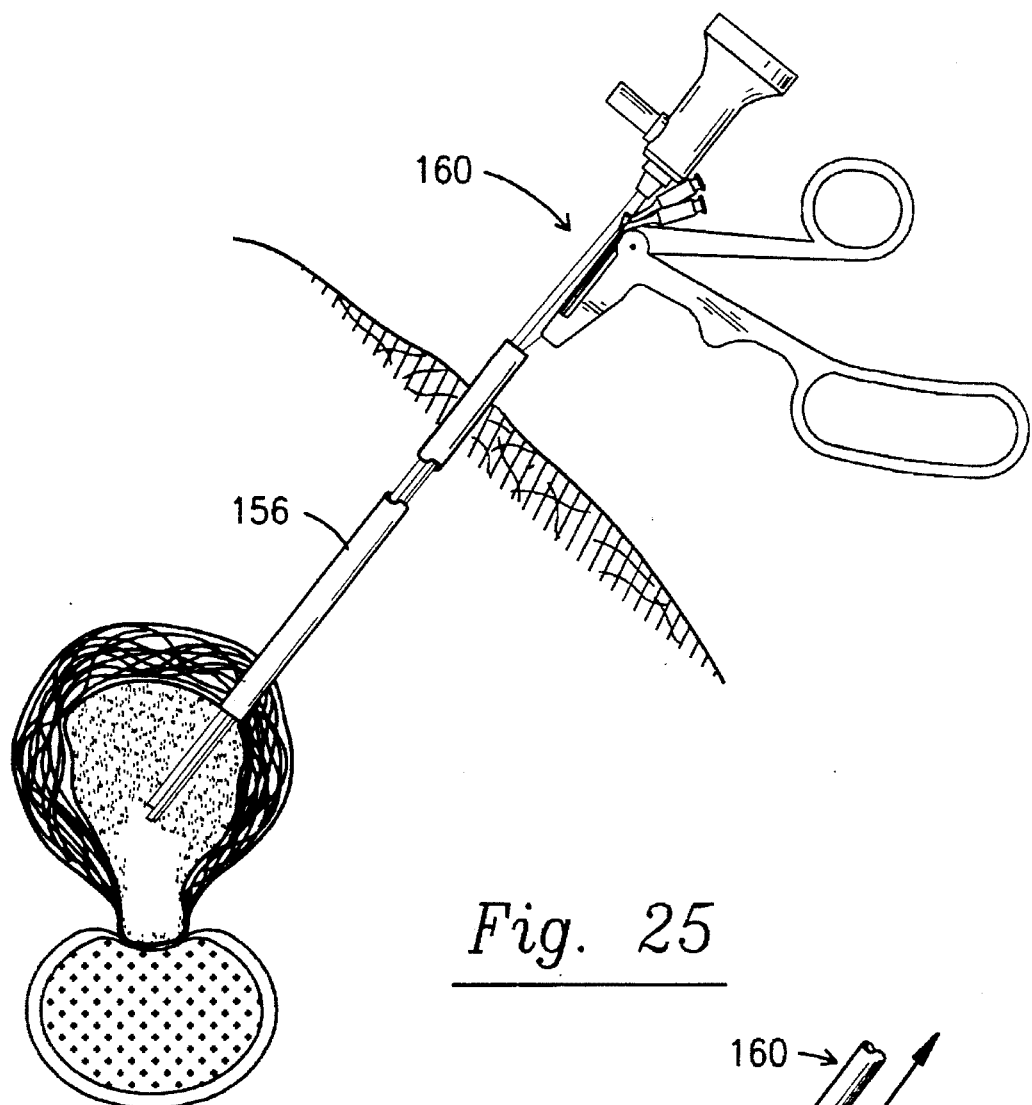
FIG. 25 is the seventh figure in said series.

FIGS. 16–18 depict a combination tool 160 that is inserted through dilator tube 156 as depicted in FIG. 25. Tool 160 includes a rod lens 162 for viewing the surgical site, optical fibers 164 for illuminating said site, irrigation tube 166 that leads rod lens 162 as shown, laser channel 168 that leads irrigation tube 166, and suction tube 170 that leads laser channel 168. This important tool 160 is more fully disclosed in a co-pending U.S. patent application, bearing Ser. No. 07/810,622 which is incorporated herein by reference. Connector 167 interconnects irrigation tube 166 to an external source of irrigation fluid. Similarly, connector 169 connects laser channel 168 to a source of coherent light, and connector 171 connects suction tube 170 to a source of negative pressure.

The novel surgical techniques made possible by the novel tools will now be disclosed. FIGS. 19–26 provide a diagrammatic animation of the steps of the novel procedure. More particularly, FIG. 19 depicts the first step of the novel procedure for debulking a tissue; stylet 11 is inserted as shown and the inner part thereof is removed therefrom. Guide wire 12, having its proximal end secured to holder 10 (see FIG. 1) is inserted into the stylet as indicated in FIG. 20, and holder 10 is then detached therefrom. Next, stylet 11 is removed, leaving guide wire 12 in the position depicted in FIG. 21. Elongate, narrow in diameter dilator tube 150 is then guided to the incision by guide wire 12; the leading end of dilator tube 150 thus dilates the incision slightly. Next, dilator tube 152, having a length less than that of tube 150, but having a greater internal and external diameter is ensleeved over tube 150 so that the leading end of tube 152 enters the incision and gradually dilates it. The same steps are followed with tubes 154 and 156; note that tube 156 has the shortest extent, and the greatest outside and inside diameter; it represents the final dilator tube and performs the function of dilating the incision to its final dilation.

Tubes 150, 152, and 154 are then removed so that only tube 156 remains in position.

Figure 23:
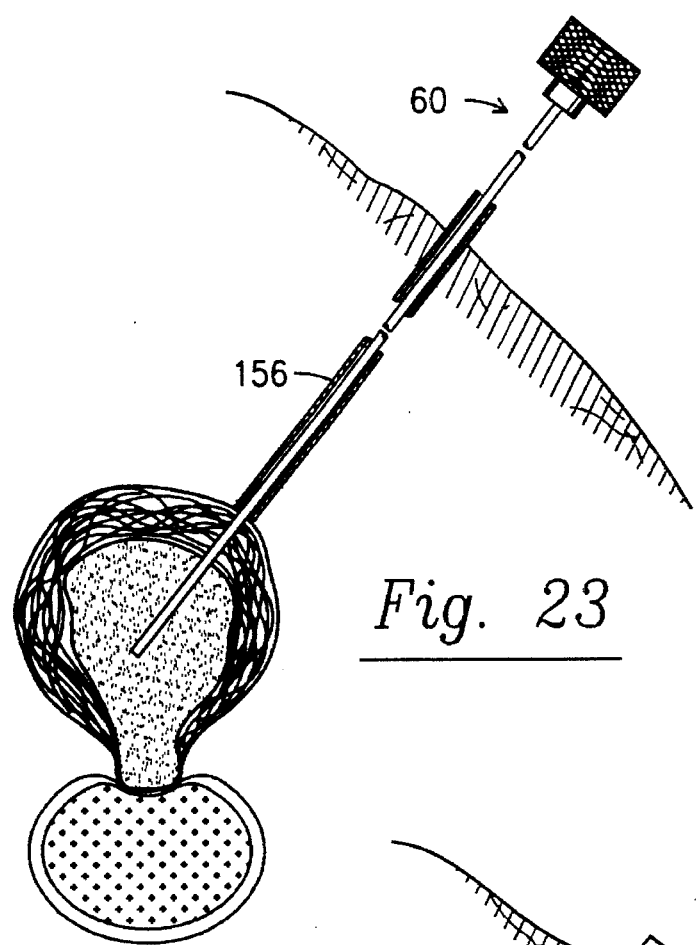
FIG. 23 is the fifth figure in said series.
Figure 24:
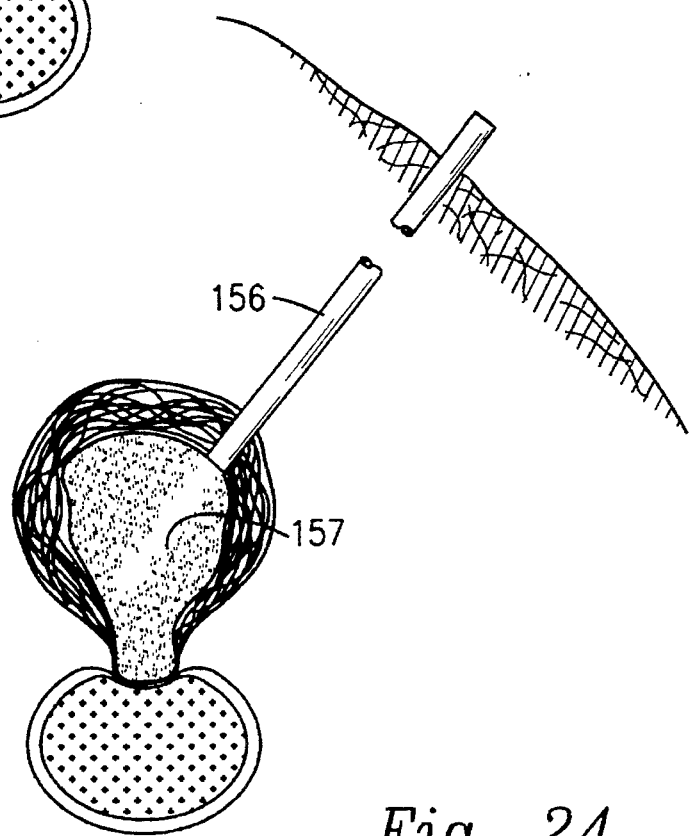
FIG. 24 is the sixth figure in said series.

Next, as depicted in FIG. 23, the ligament cutter 60 of FIG. 5 is inserted through tube 156 so that tissue cutting may begin. FIG. 24 shows bore 157 formed in the tissue after cutter 60 has been used and withdrawn from tube 156.

Combination tool 160 is then inserted through tube 156, as depicted in FIG. 25. The physician then performs the multiple functions already described.

Figure 26:
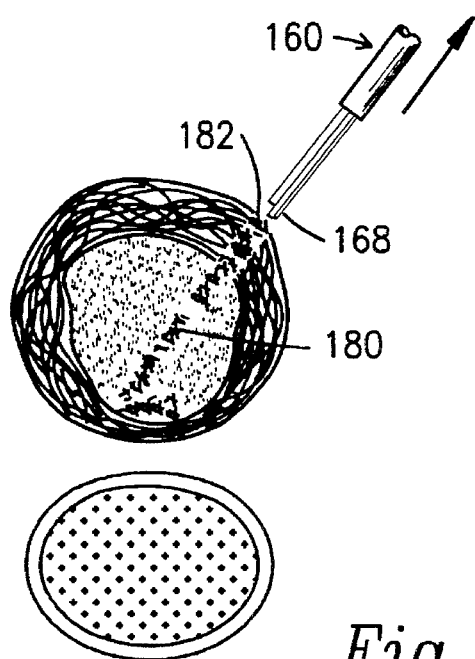
FIG. 26 is the eighth figure in said series.
Figure 20:
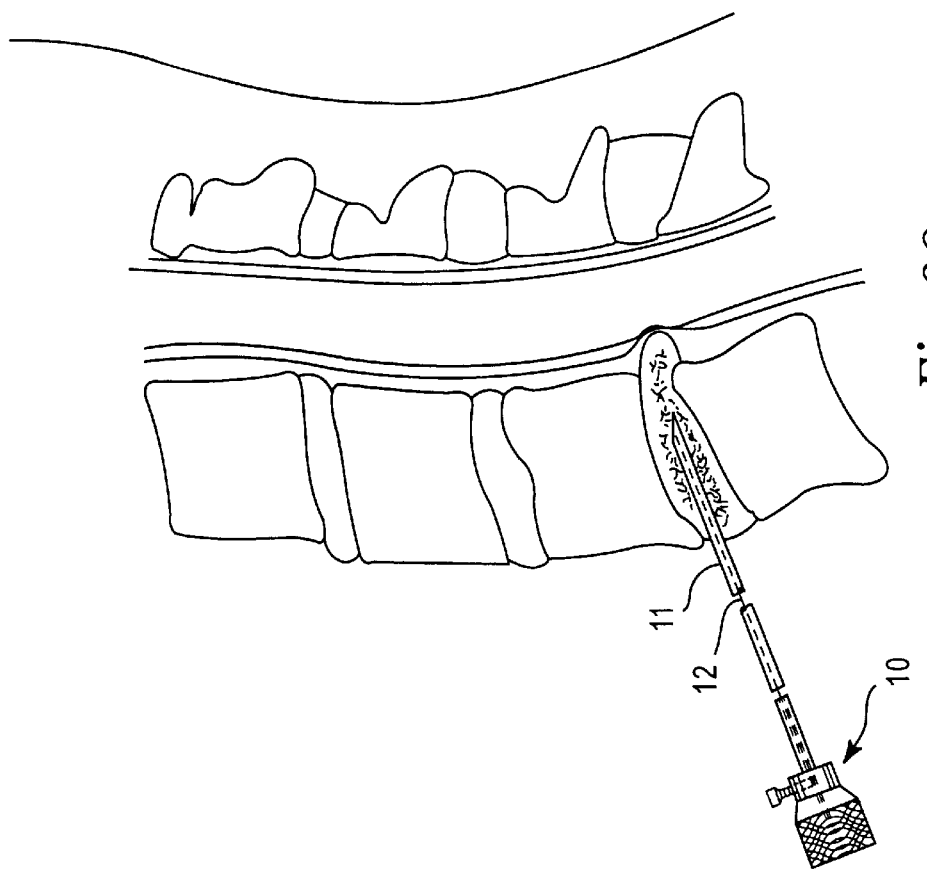

FIG. 26 indicates how tool 160 is withdrawn. Marks 180 indicate tissue that is fused together by the heat generated by laser channel 168 as tool 160 is gradually withdrawn. This prevents tissue (disc material) from escaping through annulus 182. Note by comparing FIGS. 25 and 26 that the tissue in FIG. 26 has been debulked so that the protruding disc material collapses back into the cavity formed in the disc material by tool 160. The steps of this method were also disclosed, albeit to a different extent, in U.S. patent bearing Ser. No. 07/695,633 to the present inventor; that disclosure is incorporated hereinto by reference.

This invention is clearly new and useful. Moreover, it was not obvious to those of ordinary skill in this art at the time it was made, in view of the prior art considered as a whole as required by law.

This invention pioneers the art of arthroscopic cervical discectomy instruments and methods for their use. Accordingly, the claims that follow are entitled to broad interpretation, as a matter of law, to protect from piracy the heart or essence of this breakthrough invention.

It will thus be seen that the objects set forth above, and those made apparent from the foregoing description, are efficiently attained and since certain changes may be made in the above construction without departing from the scope of the invention, it is intended that all matters contained in the foregoing construction or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,
What is claimed is:

1. A method of dilating an incision, comprising the steps of:

inserting a stylet having an inner bore and an outer barrel through said incision and withdrawing said inner bore;

providing a first tube of cylindrical construction having a first predetermined length and a first predetermined diameter;

providing a second tube of cylindrical construction having a second predetermined length greater than said first predetermined length and a second predetermined diameter less than said first predetermined diameter but greater than an outer diameter of said outer barrel so that said first tube telescopically receives said second tube and so that said second tube telescopically receives said outer barrel;

tapering a leading end of said second tube so that said leading end is easily slid into a ligament without imparting trauma to the ligament;

dilating an incision a first amount by inserting the tapered leading end of the second tube through said incision;

dilating said incision further by inserting the leading end of the first tube thereinto, said insertion being accomplished by sliding said first tube toward the incision over said second tube until the leading end of the first tube is flush with the leading end of the second tube, said second tube serving to guide the first tube to the incision; and withdrawing said second tube from the inner bore of said first tube and leaving said first tube in the incision so that subsequent surgical instruments may be introduced to a surgical site through the inner bore of said first tube.

2. A dilator tube, comprising:

an elongate tube;

a base member fixedly secured to a proximal end of said tube;

a recess of predetermined depth formed in a distal end of said base member;

a boss means formed in said distal end of said base member, said boss means having a distal end extending distally beyond the distal end of said base member and said boss means having a proximal end integral with a bottom wall of said recess; and said elongate tube having a tapered distal end to facilitate its insertion through an incision in the substantial absence of trauma to tissue.

3. A dilator means, comprising:

a first dilator tube of predetermined length;

a base member secured to a proximal end of said first dilator tube;

said first dilator tube and said base member having a common bore formed therein;

a water port formed in said base member, said water port having a bore formed therein in fluid communication with the bore common to said first dilator tube and said base member;

a recess of predetermined depth formed in a proximal end of said base member;

a second dilator tube having a predetermined length greater than the predetermined length of said first dilator tube;

said second dilator tube having an outside diameter less than said common bore so that said first dilator tube telescopically receives said second dilator tube;

a base member secured to a proximal end of said second dilator tube;

a recess of predetermined depth formed in a distal end of said second dilator tube base member;

a boss member extending from a bottom wall of said recess, said boss member extending distally beyond the distal end of said second dilator tube base member;

said boss member configured and dimensioned to be slidingly received within the recess formed in the proximal end of the first dilator tube base member;

the proximal end of said first tube dilator base member being slidingly received within the recess formed in the second dilator tube base member when said first dilator tube slidingly receives said second dilator tube;

whereby a double lock is provided to lock the first dilator tube base member to the second dilator tube base member, said first and second dilator tubes forming said dilator means when coupled together.

* * * * *

US005472426C1

(12) EX PARTE REEXAMINATION CERTIFICATE (4844th)
United States Patent
Bonati et al.

(10) Number: US 5,472,426 C1
(45) Certificate Issued: Sep. 2, 2003

(54) CERVICAL DISCECTOMY INSTRUMENTS

(75) Inventors: Alfred O. Bonati, 5420 Westshore Dr., New Port Richey, FL (US) 34652; Philip J. Ware, Spring Hill, FL (US)

(73) Assignees: B.E.I. Medical, Hackensack, NJ (US); Alfred O. Bonati, New Port Richey, FL (US); AOB Properties Limited Partnership, Hudson, FL (US)

Reexamination Request:
No. 90/006,217, Feb. 12, 2002

Reexamination Certificate for:
Patent No.: 5,472,426
Issued: Dec. 5, 1995
Appl. No.: 08/108,036
Filed: Aug. 17, 1993

Related U.S. Application Data

(63) Continuation-in-part of application No. 07/758,013, filed on Sep. 12, 1999, now Pat. No. 5,269,797.

(51) Int. Cl.$^7$ .................. A61M 5/178; A61M 29/00; A61B 10/00
(52) U.S. Cl. .................. 604/164.1; 606/191; 600/564
(58) Field of Search .................. 604/158–166; 606/79, 167, 170, 185, 191, 193, 194, 197–199; 600/564

(56) References Cited

U.S. PATENT DOCUMENTS

| | | | |
|---|---|---|---|
| 3,858,577 A | | 1/1975 | Bass et al. |
| 4,146,019 A | | 3/1979 | Bass et al. |
| 4,313,431 A | | 2/1982 | Frank |
| 4,418,688 A | | 12/1983 | Loeb |
| 4,449,532 A | * | 5/1984 | Storz ............... 606/191 |
| 4,470,407 A | | 9/1984 | Hussein |
| 4,517,977 A | | 5/1985 | Frost |
| 4,522,206 A | | 6/1985 | Whipple et al. |
| 4,545,374 A | | 10/1985 | Jacobson |
| 4,551,129 A | | 11/1985 | Coleman et al. |
| 4,573,448 A | * | 3/1986 | Kambin ............... 128/1 |
| 4,586,491 A | | 5/1986 | Carpenter |
| 4,601,290 A | | 7/1986 | Effron et al. |
| 4,603,694 A | | 8/1986 | Wheeler |
| 4,678,459 A | | 7/1987 | Onik et al. |
| 4,782,819 A | | 11/1988 | Adair |
| 4,802,461 A | | 2/1989 | Cho |
| 4,819,635 A | | 4/1989 | Shapiro |
| 4,850,351 A | | 7/1989 | Herman et al. |
| 4,905,082 A | | 2/1990 | Nishigaki et al. |
| 4,919,113 A | | 4/1990 | Sakamoto et al. |

(List continued on next page.)

FOREIGN PATENT DOCUMENTS

| | | |
|---|---|---|
| EP | 0 174 084 | 3/1986 |
| EP | 0 402 101 | 5/1990 |
| EP | 0 438 353 A1 | 1/1991 |

OTHER PUBLICATIONS

Abstract; Orthopade (1996) Feb. 25 (1): 42–8; Siebert WE, Berendsen BT, Tollgaard J.

(List continued on next page.)

Primary Examiner—Michael J Hayes

(57) ABSTRACT

Arthroscopic cervical discectomy instruments include a push knob for a guide wire, a pair of telescopically mounted dilator tubes, one of which includes a water port so that the tube provides the additional function of an irrigation tube, a ligament cutter, a continuous suction punch, a cervical osteotone, a cervical cureet, a nucleus extractor and a cureet nucleus extractor. The dilator tubes, the ligament cutter, and the continuous suction punch are all centrally bored to receive the guide wire. All of the instruments are of arthroscopic proportions and each instrument, exclusive of its handle, is slideably insertable through the bore of the largest in diameter dilator tube. The largest in diameter dilator tube serves as a dilator, an irrigation tube, and as the main sheath through which the other tools are inserted. In a second embodiment, the pair of dilator tubes are replaced with a plurality of telescoping dilator tubes of progressively larger diameters and shorter lengths. The tools enable a novel dilation method and a novel surgical method.

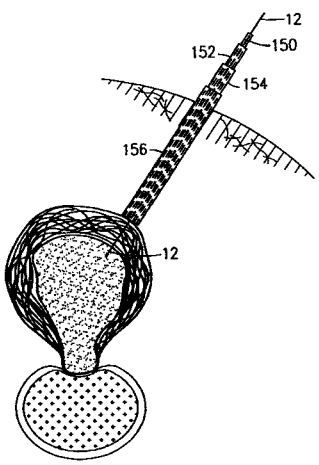

U.S. PATENT DOCUMENTS

| | | | |
|---|---|---|---|
| 4,922,902 | A | 5/1990 | Wuchinich et al. |
| RE33,258 | E | 7/1990 | Onik et al. |
| 4,950,278 | A | 8/1990 | Sachse et al. |
| 4,963,142 | A | 10/1990 | Loertscher |
| 5,055,100 | A | 10/1991 | Olsen |
| 5,083,549 | A | 1/1992 | Cho et al. |
| 5,131,382 | A | 7/1992 | Meyer |
| 5,140,984 | A | 8/1992 | Dew et al. |
| 5,169,396 | A | 12/1992 | Dowlatshahi et al. |
| 5,195,541 | A | 3/1993 | Obenchain |
| 5,201,729 | A | 4/1993 | Hertzmann et al. |
| 5,242,439 | A | 9/1993 | Larsen et al. |
| 5,267,996 | A | 12/1993 | Fletcher |
| 5,275,609 | A | 1/1994 | Pingleton et al. |
| 5,285,795 | A | 2/1994 | Ryan et al. |
| 5,290,303 | A | 3/1994 | Pingleton et al. |
| 5,324,254 | A | 6/1994 | Phillips |
| 5,395,317 | A | 3/1995 | Kambin |
| 5,403,276 | A | 4/1995 | Schechter et al. |
| 5,425,355 | A | 6/1995 | Kulick |
| 5,443,448 | A * | 8/1995 | DeVries .................. 604/96.01 |
| 5,468,238 | A | 11/1995 | Mersch |
| 5,489,290 | A | 2/1996 | Furnish |
| 5,505,210 | A | 4/1996 | Clement |

OTHER PUBLICATIONS

Abstract; Regan, JF, McAfee, PC, Evolution of Minimally Invasive Surgery, Atlas of Endoscopic Spine Surgery, 1995.

Acta Orthop Scand Suppl 1993; 251:38–44; Lasers in percutaneous disc surgery; Mayer HM, Muller G, Schwetlick G., Title and Author submitted.

J Clin Laser Med Surg 1993 Aug; 11(4): 181–3; Percutaneous laser disc decomposition (PLDD) update: focus on device and procedure advances; Choy DS, Abstract submitted.

Zhonghua Wai Ke Za Zhi 1993 Jul.; 31(7): 407–10; Percutaneous laser disc decomposition: an experimental study; Qi Q., Abstract submitted.

J. Clin Laser Med Surg 1992 Dec; 10(6):435–7; In vitro and in vivo fall of intradiscal pressure with laser disc decompression; Choy DS, Diwan S., Abstract.

Todays OR Nurse 1992 Nov; 14(11):3–6; Laser disc decompression; Weak SA, Abstract.

Orthopade 1992 Aug; 21(4): 267–72; Endoscopy of the spine: minimally invasive therapy; Article in German; Leu H, Schreiber A, Abstract.

Spine 1992 Aug; 17(8): 949–56; Erratum in; Spine 1993 Jun. 1:18(7):939; percutaneous laser disc decompression. A new therapeutic modality,; Choy DS, Ascher PW, Ranu HS, Saddekni S, Alkaitis D, Liebler W, Hughes J. Diwan S, Altman P, Abstract.

J Clin Med Surg 1992 Jun.; 10(3): 177–84; Percutaneous laser disc decompression: an update—Spring 1992; Choy DS, Michelsen J, Getrajdman G, Diwan S, Abstract.

J Fla Med Assoc 1992 Jan.; 79(1):37–9; Early experience with laser disc decompression. A percutaneous method; Davis JK, Abstract.

Acta Neurochir Suppl (Wien) 1992;54:53–8; Percutaneous endoscopic laser discectomy (PELD). A new surgical technique for non–sequestrated lumbar discs; Mayer HM, Brock M, Berlien HP, Weber B, Abstract.

Mt Sinai J Med 1991 Mar.; 58(2):159–64; Arthroscopic mecrodiskectomy; Kambin P, Abstract.

No Skinkel Geka 1991 May; 19(5):429–34; Clinical analysis of 270 cases of microsurgical lumbar discectomy; Hanakita J, Suwa H, Nishihara K, Iihara K, Sakaida H, Nishi S., Abstract.

Neuroradiology 1991; 33(5):407–10; Lumbar percutaneous discectomy, Initial experience in 28 cases; Faubert C, Caspar W., Abstract.

Ital J. Orthop Traumatol 1991 Mar.; 17(1):5–21; The Onik method of automated percutaneous lumbar diskectomy (A.P.L.D.). Criteria of selection, technique, and evaluation of results; Bocchi L, Ferrata P, Passarello F., Abstract.

Spine 1991 Mar.;16(3):359–63; Automated percutaneous discectomy; Davis GW, Onik G, Helms C Abstract.

Neuroradiology 1991; 33(6):516–9; Percutaneous discectomy using Onik's method: 3 years' experience; Bonaldi G, Belloni G, Prosetti D, Moschini L, Abstract.

Clin Laser Mon 1990 Jul.;8(7):105–6; Percutaneous discectomy improved with KTP laser; Davis JK Title and Author submitted.

Clin Orthop 1989 Jan.;(238):64–70; Percutaneous automated discectomy. A new approach to lumbar surgery; Maroon JC, Onik G, Sternau L. Abstract.

Clin Orthop 1989 Jan.;50–5; Erratum in: Clin Orthop 1989 Nov;(248):311; Early experience with percutaneous lateral discectomy; Stern MB, Abstract.

Clin Orthop 1989 Jan.;(238):71–6; Automated percutaneous discectomy at the L5–S1 level. Use of a curved cannula; Onlik G, Maroon J, Davis GW; Allegheny–Singer Research Institute, Pittsburh, PA, Abstract.

Skeletal Radiol 1989; 18(8):579–83; Automated percutaneous lumbar discectomy; Helms CA, Onik G, David GW, Abstract.

Acta Neurochir Supp (Wien) 1988;43:58–62; Automated percutaneous discectomy; preliminary experience; Onik G, Maroon J, Day A, Helms C, Abstract.

Ital J Orthop Traumatol 1988 Dec.14(4):443–54; Percutaneous lumbar nuclectomy according to the Onik method: indications, technique, first results; Solini A, Orsini G, Paschero B, Abstract.

Chin Orthop 1987 Oct.;(223):145–54; Percutaneous posterolateral discectomy. Anatomy and mechanism; Kambin P, Brager MD, Abstract.

J Neurosurg 1987 Jul.;67(1):150–2; Percutaneous discectomy; Fager CA Title and Author submitted.

N Engl Med 1987 Sep. 17;317(12):771–2; Related Articles, Books, LinkOut; Percutaneous laser neculeolysis of lumbar disks; Choy DS, Case RB, Fielding W, Hughes J, Liebler W, Ascher P, Title and Abstract.

Geriatrics 1984 Aug.;39(8):41–2, 45, 48 passim; New techniques for treatment of disk disease; Friedman WA Title and Author submitted.

* cited by examiner

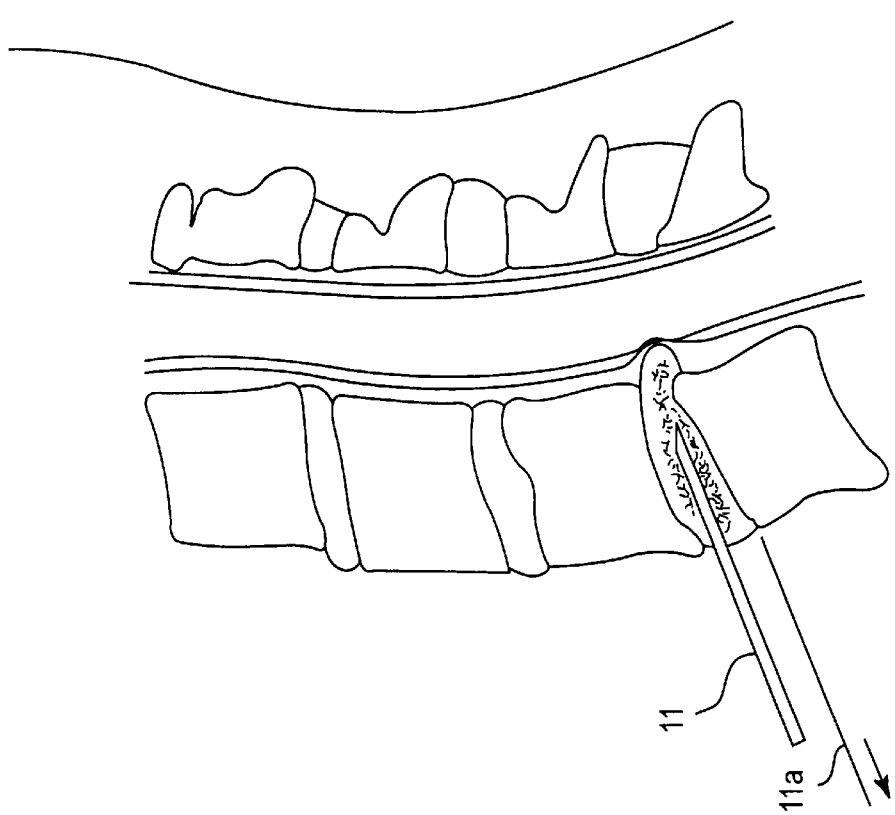
*Fig.19*
(AMENDED)

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicated additions made to the patent.

THE DRAWING FIGURES HAVE BEEN CHANGED AS FOLLOWS:

An inner part 11a and legend "Amended" have been added to FIG. 19.

ONLY THOSE PARAGRAPHS OF THE SPECIFICATION AFFECTED BY AMENDMENT ARE PRINTED HEREIN.

Column 1, lines 6–9:

This [disclosure] *application* is a continuation-in-part of a disclosure filed Sep. 12, 1991, bearing Ser. No. 07/758,013, by the same inventors, now U.S. Pat. No. 5,269,797, entitled "Cervical Discectomy Instruments[.]*,*" *and is also a continuation-in-part of U.S. Pat. No. 5,290,279, filed May 17, 1993 by the same inventors, entitled "Arthroscopic Tool Combining Five Functions in One," which is a continuation-in-part of Application Ser. No. 07/810,622, filed Dec. 19, 1991, by the same inventors, which is now abandoned.*

Column 8, line 58–Column 9, line 11:

The novel surgical techniques made possible by the novel tools will now be disclosed. FIGS. 19–26 provide a diagrammatic animation of the steps of the novel procedure. More particularly, FIG. 19 depicts the first step of the novel procedure for debulking a tissue; stylet 11 is inserted as shown and the inner *tube or* part 11a thereof is removed therefrom. Guide wire 12, having its proximal end secured to holder 10 (see FIG. 1) is inserted into the stylet as indicated in FIG. 20, and holder 10 is then detached therefrom. Next, stylet 11 is removed, leaving guide wire 12 in the position depicted in FIG. 21. Elongate, narrow in diameter dilator tube 150 is then guided to the incision by guide wire 12; the leading end of dilator tube 150 thus dilates the incision slightly. Next, dilator tube 152, having a length less than that of tube 150, but having a greater internal and external diameter is ensleeved over tube 150 so that the leading end of tube 152 enters the incision and gradually dilates it. The same steps are followed with tubes 154 and 156; note that tube 156 has the shortest extent, and the greatest outside and inside diameter; it represents the final dilator tube and performs the function of dilating the incision to its final dilation.

AS A RESULT OF REEXAMINATION, IT HAS BEEN DETERMINED THAT:

The patentability of claims 2 and 3 is confirmed.

Claim 1 is determined to be patentable as amended.

New claims 4 and 5 are added and determined to be patentable.

1. A method of dilating an incision, comprising the steps of:

inserting a stylet having an inner bore, *an inner tube disposed within said inner bore*, and an outer barrel through said incision and withdrawing said inner [bore] *tube*;

providing a first tube of cylindrical construction having a first predetermined length and a first predetermined diameter;

providing a second tube of cylindrical construction having a second predetermined length greater than said first predetermined length and a second predetermined diameter less than said first predetermined diameter but greater than an outer diameter of said outer barrel so that said first tube telescopically receives said second tube and so that said second tube telescopically receives said outer barrel;

*providing a combination tool having a rod lens for viewing a surgical site, optical fibers for illuminating said surgical site, an irrigation tube, a laser channel, and a suction tube;* tapering a leading end of said second tube so that said leading end is easily slid into a ligament without imparting trauma to the ligament;

dilating an incision a first amount by inserting the tapered leading end of the second tube through said incision;

dilating said incision further by inserting the leading end of the first tube thereinto, said insertion being accomplished by sliding said first tube toward the incision over said second tube until the leading end of the first tube is flush with the leading end of the second tube, said second tube serving to guide the first tube to the incision; [and]

withdrawing said second tube from the inner bore of said first tube and leaving said first tube in the incision so that subsequent surgical instruments may be introduced to a surgical site through the inner bore of said first tube*; and*

*inserting said combination tool into said first tube in order to perform arthroscopic discectomy at the surgical site.*

*4. A method of dilating an incision, comprising the steps of:*

*inserting a stylet having an inner bore, an inner tube disposed within said inner bore, and an outer barrel through said incision and withdrawing said inner tube;*

*inserting a guide wire into said inner bore of said stylet into a ligament or bone;*

*removing said stylet;*

*providing a first tube of cylindrical construction having a first predetermined length and a first predetermined diameter;*

*providing a second tube of cylindrical construction having a tapered leading end so that said leading end is easily slid into a ligament without imparting trauma to the ligament, said second tube having a second predetermined length greater than said first predetermined length and a second predetermined diameter less than said first predetermined diameter but greater than an outer diameter of said outer barrel so that said first tube telescopically receives said second tube and so that said second tube telescopically receives said outer barrel;*

*providing a combination tool having a rod lens for viewing a surgical site, optical fibers for illuminating said surgical site, an irrigation tube, a laser channel, and a suction tube;*

*dilating an incision a first amount by inserting the tapered leading end of the second tube through said incision;*

*dilating said incision further by inserting the leading end of the first tube thereinto, said insertion being accom-* plished by sliding said first tube toward the incision over said second tube until the leading end of the first tube is flush with the leading end of the second tube, said second tube serving to guide the first tube to the incision;

withdrawing said second tube from the inner bore of said first tube and leaving said first tube in the incision so that subsequent surgical instruments may be introduced to a surgical site through the inner bore of said first tube; and inserting said combination tool into said second tube in order to perform arthroscopic discectomy at the surgical site.

5. A method of dilating an incision, comprising the steps of:

(a) inserting a stylet having an inner tube and an outer barrel through said incision and withdrawing said inner tube;

(b) providing a plurality of tubes in an order from a first tube to a last tube, each tube being of cylindrical construction each and having a fixed length, a fixed inner diameter, and a fixed outer diameter, the length of each of said plurality of tubes in the order being progressively shorter from said first tube to said last tube a previous tube in said order, and the inner diameter of each of said plurality of tubes in the order being larger than the outer diameter of a previous tube in the order, from the first tube to the last tube in the order, respectively, the first tube having a predetermined outer diameter, such that the plurality of tubes from the first tube to the last tube telescopically receives a next tube in the order over top said previous tube, a leading end of the first tube being tapered so that said leading end is easily slid into a ligament without imparting trauma to the ligament, said first tube being a narrowest and longest tube of said plurality of tubes, wherein said stylet is received in said first tube;

(c) providing a combination tool having a rod lens for viewing a surgical site, optical fibers for illuminating said surgical site, an irrigation tube, a laser channel, and a suction tube;

(d) dilating an incision a first amount by inserting the tapered leading end of the first tube through said incision;

(e) dilating said incision further by inserting the leading end of a next tube in said order over said first tube, said insertion being accomplished by sliding said next tube toward the incision over said first tube until the leading end of the next tube is flush with the leading end of the first tube, said second tube serving to guide the first tube to the incision;

(f) withdrawing said first tube from the inner bore of said first tube;

(g) dilating said incision further by repeating steps (e) and (f) for each next tube of said plurality of tubes and leaving a last tube in the incision so that subsequent surgical instruments may be introduced to a surgical site through an inner bore of said last tube; and (h) inserting said combination tool into said last tube in order to perform arthroscopic discectomy at the surgical site.

\* \* \* \* \*